United States Patent
Bengs et al.

(10) Patent No.: US 6,696,563 B2
(45) Date of Patent: Feb. 24, 2004

(54) α-AMYLASE-RESISTANT POLYSACCHARIDES, PRODUCTION METHOD, USE AND FOODS CONTAINING THESE POLYSACCHARIDES

(75) Inventors: Holger Bengs, Frankfurt am Main (DE); Gisela Jacobasch, Wandlitz (DE); Detlef Schmiedl, Berlin (DE); Jörg Riesmeier, Berlin (DE); Martin Quanz, Berlin (DE); Michael Bäuerlein, Berlin (DE); Nicholas Provart, Berlin (DE)

(73) Assignee: Celanese Ventures GmbH (DE)

( * ) Notice: Subject to any disclaimer, the term of this patent is extended or adjusted under 35 U.S.C. 154(b) by 8 days.

(21) Appl. No.: 09/741,143

(22) Filed: Dec. 21, 2000

(65) Prior Publication Data

US 2003/0004332 A1 Jan. 2, 2003

Related U.S. Application Data

(63) Continuation of application No. PCT/EP99/04129, filed on Jun. 15, 1999.

(30) Foreign Application Priority Data

Jul. 9, 1998 (DE) .......................................... 198 30 618

(51) Int. Cl.⁷ .................................................. C07H 1/00
(52) U.S. Cl. .................... 536/123.12; 536/2; 536/18.5; 536/102; 536/106; 536/123.1; 536/124; 536/127; 536/128
(58) Field of Search .......................... 536/2, 18.5, 102, 536/106, 123.1, 123.12, 124, 127, 128

(56) References Cited

U.S. PATENT DOCUMENTS

| | | | | | |
|---|---|---|---|---|---|
| 5,855,946 | A | * | 1/1999 | Seib et al. | 426/549 |
| 6,013,299 | A | * | 1/2000 | Haynes et al. | 426/549 |
| 6,043,229 | A | * | 5/2000 | Kettlitz et al. | 514/60 |

FOREIGN PATENT DOCUMENTS

| | | | |
|---|---|---|---|
| DE | EP0/688/872 A1 | * | 12/1995 |
| EP | 93104776.5 | | 3/1993 |
| EP | PCT/EP95/01893 | | 5/1995 |
| US | PCT/US90/03205 | | 6/1990 |
| US | PCT/US98/10786 | | 5/1998 |

OTHER PUBLICATIONS

H.N. Englyst, S.M. Kingman and J.H. Cummings, Classification and measurement of nutrionally important starch fractions, 1992, pp. S33–S50, vol. 46 (Suppl.), *European Journal of Clinical Nutrition*.

* cited by examiner

*Primary Examiner*—James O. Wilson
*Assistant Examiner*—Patrick Lewis
(74) *Attorney, Agent, or Firm*—Gilberto M. Villacorta; Serge Sira; Katten Muchin Zavis Rosenman

(57) ABSTRACT

The invention relates to a production method of α-amylase resistant polysaccharides with high RS content, comprising the following steps: a) producing a paste of water-insoluble poly-(1,4-α-D-glucan) and water; b) heating the paste; c) cooling off and retrogradation of the past at a temperature that is lower than the temperature of the heated paste and d) optionally drying the resulting product.

19 Claims, 1 Drawing Sheet

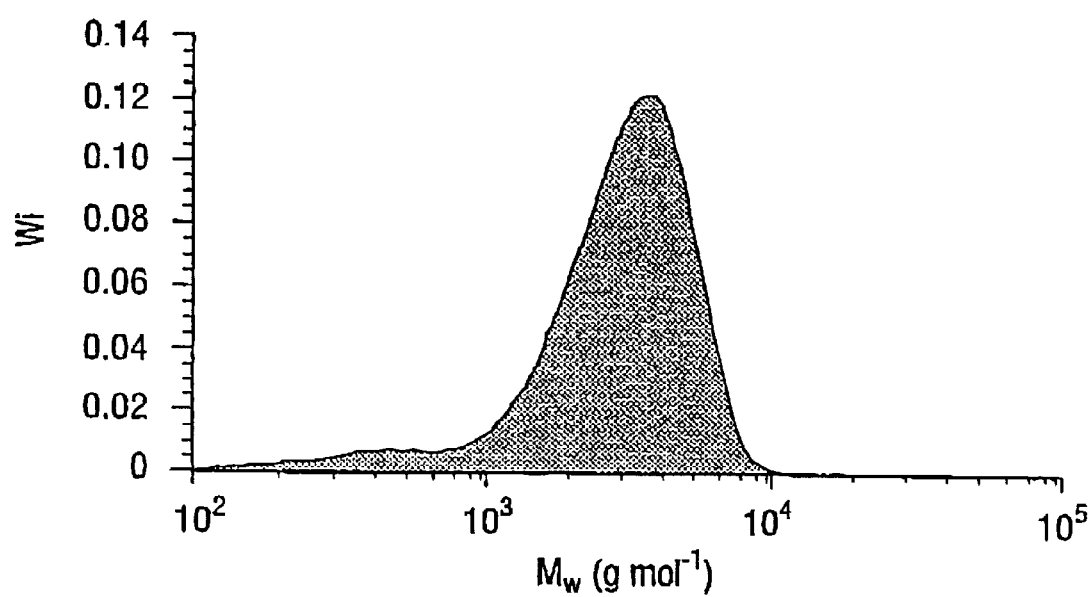
Fig. 1 GPC chromatogram of the poly(1,4-α-D-glucan)

α-AMYLASE-RESISTANT POLYSACCHARIDES, PRODUCTION METHOD, USE AND FOODS CONTAINING THESE POLYSACCHARIDES

RELATED APPLICATIONS

This application is a continuation of International Application Number PCT/EP99/04129, filed Jun. 15, 1999, which in turn claims priority from German Patent Application No. 198 30 618.0, filed Jul. 9, 1998, both of which are incorporated herein by reference.

BACKGROUND OF THE INVENTION

The use of resistant starches (RS) is of increasing importance for the food Industry. The breakdown of RS products only produces a small amount of energy for the organism. This energy supply is related solely to the oxidative breakdown of absorbed short-chain fatty acids from the large intestine. These short-chain fatty acids are end products of the carbohydrate metabolism of the intestinal microflora. Two functions are linked with the intake of RS-containing foods: provision of substrate for energy metabolism of the intestinal microflora and for that of the large intestine epithelial cells. The latter, to maintain their structure and function, are dependent on a luminal feed of short-chain fatty acids, in particular butyrate.

It has long been known that the content of highly branched amylopectin in starches, which usually consist of amylose and amylopectin of varying composition, can be reduced by specific enzymatic treatment, as a result of which the content of short-chain amylose structures can be increased (U.S. Pat. No. 3,729,380). It is also known that such products have a greater tendency to retrogradation than native starches. In this process, α-amylase-resistant starch structures develop. Resistant starches (RS) are carbohydrate polymers which are not broken down by α-amylase. As a result they are a reduced-energy component providing body in food compositions, within the meaning of a dietary fiber. For technical reasons, the treatment with debranching enzymes usually takes place in a not-too-concentrated aqueous starch gel.

EP 0 564 893 A1 describes and claims a process for producing an RS product which contains up to 15% RS. This process is characterized in that the aqueous suspension of a starch which contains at least 40% amylose is gelatinized and enzymatically debranched by treatment with an enzyme which opens the α-1,6-glycosidic bonds, and the resultant intermediate product is then retrograded. According to EP 0 564 893 A1, the optimum starch concentration in the suspension is 15% and the examples of this EP patent application illustrate the process when the starch concentrations are either reduced to 14% or increased to 17%. The starting material contains at least 40% amylose and Is a corn starch. It is further shown that at an amylose content of 25%, no resistant starch (RS) is formed by this process. In addition, it was found that when the amylose content is increased above 40% to up to 100%, a product can be generated which contains up to 50.3% RS.

EP 0 688 872 A1 describes and claims a process for producing an RS-containing product which contains from 25 to 50% by weight of RS. According to the specifications, EP 0 688 872 A1 describes and claims a process for producing an RS-containing product in which an aqueous suspension of a partially degraded gelatinized starch is enzymatically debranched and the intermediate product is retrograded.

(In this context, "partially degraded starch" is taken to mean a polymer whose molecular weight has been decreased by suitable treatment, the shortening of the chain length affecting both the amylose and the amylopectin. The degradation includes not only hydrolytic processes (acid- or enzyme-catalyzed) but also extrusion, oxidation or pyrolysis).

Acid-degraded root or tuber starches and maltodextrins of root or tuber starches are particularly emphasized. Maltodextrins are characterized by a DE value (DE: dextrose equivalent) in the range from 1 to 19.

They are produced from potato starch or tapioca starch which contain up to 25% amylose, The aqueous suspension of such maltodextrins has a solids content of 20% by weight or more for the process. The maltodextrins are further characterized in that they have high contents of oligomers having degrees of polymerization less than 10 (DP<10) of up to 22% by weight and a mean molecular weight of $1.3680 \times 10^4$ g/mol. The debranching enzymes which are used for the known process are pullulanase and isoamylase. At the end of the enzymatic treatment, retrogradation in a temperature range from 0 to 30° C. is carried out in a time period of from 1 to 3 days, by allowing the aqueous reaction product to stand. The product is then dried by spray-drying. A pulverulent product having an RS content up to a maximum of 60% by weight is produced.

BRIEF SUMMARY OF THE INVENTION

The inventive description serves the purpose of producing economically carbohydrate polymers having a high content of resistant, relatively thermally stable structures in order to be able to use them in food manufacture.

Thus one embodiment of the invention relates to α-amylase-resistant polysaccharides which are poly(1,4-α-D-glucans), characterized in that they have an RS content of at least 65% by weight.

In connection with the present invention, an RS content is taken to mean the content of α-amylase-resistant polysaccharides, as can be determined by the method of Englyst et al. (Classification and measurement of nutritionally important starch Fractions, European Journal of Clinical Nutrition, 46 (Suppl. 23) (1992) 33–50); see also example 3.

The inventive α-amylase-resistant polysaccharides can be characterized by an RS content of at least 75, and in particular at least 95% by weight.

In addition, the inventive α-amylase-resistant polysaccharides can be characterized in that the poly(1,4-α-D-glucans) are chemically modified in a manner known per se.

Thus, the poly(1,4-α-D-glucans) can have been chemically modified by etherification or esterification in the 2, 3 or 6 position. Those skilled in the art have long been familiar with chemical modification; see, for example, the following references:

1. Functional Properties of Food Components, $2^{nd}$ edition, Y. Pomeranz, Academic Press (1991)
2. Lehrbuch der Lebensmittelchemie [Textbook of food chemistry], Belitz & Grosch, Springer Verlag (1992)
3. Citrat Starch Possible Application as Resistent Starch in Different Food Systems, B. Wepner et al., European Air Concerted Action, Abstract: air3 ct94-2203, Functional Properties of Non-digestible Carbohydrates, Pro Fibre Symposium, Lisbon, February 1998, page 59.

In addition, the inventive α-amylase-resistant polysaccharides can be characterized in that they have a degree of branching in the 6 position of at most 0.5%.

In addition, the inventive α-amylase-resistant polysaccharides can be characterized in that they have a degree of branching In the 2 and/or 3 position of, in each case, at most 1.0%, and in particular at most 0.5%.

In addition, the α-amylase-resistant polysaccharides can be characterized in that the poly(1,4α-D-glucans) have a molecular weight of from $0.75 \times 10^2$ to $10^7$, preferably from $10^3$ to $10^6$, and preferably from $10^3$ to $5 \times 10^5$ g/mol and/or are water-insoluble.

In addition, the inventive α-amylase-resistant polysaccharides can be characterized in that the poly(1,4-α-D-glucans) have neither been debranched, in particular have neither been enzymatically debranched, nor have been reduced with respect to their chain length (and thus with respect to their molecular weight), in particular not by enzyme catalysis, acid catalysis, extrusion, oxidation or pyrolysis.

In addition, the inventive α-amylase-resistant polysaccardes can be obtainable by a process comprising the following steps:

a) producing a suspension or dispersion from water-insoluble poly(1,4-α-D-glucans) and water;

b) warming the suspension or dispersion;

c) cooling the resultant gel and retrogradation of the gel at a temperature which is lower than the temperature of the heated gel; and d) if appropriate drying the resultant product.

BRIEF DESCRIPTION OF THE DRAWINGS

FIG. 1 shows a GPC chromatogram of the poly(1,4-α-D-glucan) of the present invention.

DETAILED DESCRIPTION OF THE INVENTION

The term "water-insoluble" is taken to mean compounds which, according to the definition of the Deutsches Arzneimittelbuch [German pharmacopoeia] (Wissenschaftliche Verlagsgesellschaft/Stuttgart & Gori-Verlag/Frankfurt, $9^{th}$ edition, 1987; see also examples 22 to 23), come under the category of "sparingly soluble" compounds, "very sparingly soluble" or "virtually insoluble" compounds.

Those skilled in the art are familiar with the terms "suspension" and "dispersion". Supplementary reference is also made to Römpp, Chemle-Lexikon [Chemistry lexicon], $9^{th}$ edition, Thieme-Verlag, Stuttgart & New York, pages 4401 and 1010.

Those skilled in the art are also familiar with the term "gel". Supplementary reference is made to Römpp, Chemie-Lexikon [Chemistry lexicon], $9^{th}$ edition, Thieme-Veriag, Stuttgart & New York, page 2256.

In addition, the inventive α-amylase-resistant polysaccharides can be obtainable by a process comprising the following steps:

a) producing a suspension or dispersion from water-insoluble poly(1,4-α-D-glucans) and water;

b) freezing the resultant suspension or dispersion;

c) retrogradation;

d) thawing the mass obtained by step c); and e) if appropriate drying the mass obtained by step d) or dewatering the resultant mass.

A further embodiment of the invention relates to a process for producing α-amylase-resistant polysaccharides having a high RS content comprising the following steps:

a) producing a suspension or dispersion from water-insoluble poly(1,4-α-D-glucans) and water;

b) warming the suspension or dispersion;

c) cooling the resultant gel and retrogradation of the gel at a temperature which is lower than the temperature of the heated gel; and d) If appropriate drying the resultant product.

The advantage of the inventive process can be that, from the above-described starting materials, an aqueous hot gel can be produced which has solid contents up to, for example, 30% by weight or more, without, for example, debranching or partial degradation or a chain-length reduction of the starting materials used needing to be performed. This leads to a simplification of the process sequence and thus to a reduction in the costs of the process, because the time-consuming and costly use of debranching enzymes or degrading chemicals is avoided.

The inventive process can be characterized in that, in step (a), a gel having a polysaccharide content of at least about 5, and up to about 30, 35, 40, 45 or 50% by weight is produced.

In addition, the inventive process can be characterized in that, in step (b), the gel is warmed or heated to a temperature in the range from room temperature, 50, 60 or 70 to 100° C.

In addition, the inventive process can be characterized in that, in step (c), retrogradation is carried out (i) at a temperature in the range from 50°°C. to freezing point, preferably from 35 to 15° C., from 27 to 22° C., from 16 to 0° C. or from 6 to 2° C. and/or (ii) for a time interval of from 1 to 72 h, preferably from 1 to 36 h and in particular from 15 to 30 h.

In addition, the inventive process can be characterized in that, in step (c), cooling and retrogradation are carried out according to a temperature-step program (i) in a temperature range from 100 to 0° C., and preferably from 90 to 4° C.

(ii) for a total time interval of from 8 to 36 h, preferably from 20 to 28 h, and in particular from 22 to 26 h, according to the temperature-time program below stepwise and if appropriate under the action of shear forces, in which case the time intervals selected add up to a total time interval specified above:

| Temperature-time program | |
|---|---|
| Temperature (° C.) | Time interval |
| 90 ± 10 | 5 min ± 5 min |
| 80 ± 10 | 10 min ± 10 min |
| 70 ± 10 | (30 to 180 min) ±30 min |
| 40 ± 10 | (60 to 180 min) ±60 min |
| 25 ± 10 | 22 h ± 15 h |
| 4 ± 10 | 20 h ± 15 h |

A further embodiment of the invention relates to a process for producing α-amylase-resistant polysaccharides having a high RS content, comprising the following steps a) producing a suspension or dispersion from water-insoluble poly(1,4-α-D-glucans) and water;

b) freezing the resultant suspension or dispersion;

c) retrogradation;

d) thawing the mass obtained by step c); and e) if appropriate drying the mass obtained by step d) or dewatering the resultant mass.

The inventive process can be characterized in that the mass thawed according to step (d) can be subjected once more or repeatedly to steps (b) to (d), before finally thawing, drying or dewatering.

In addition, the inventive process can be characterized in that, in step (b), the resultant suspension or dispersion is cooled to a temperature in the range from 0° C. to 80° C.

In addition, the inventive process can be characterized in that, in step (c). retrogradation is carried out for a time interval of from 1 to 72 h, preferably from 1 to 36 h, and in particular from 15 to 30 h.

The embodiments of the inventive process can be characterized in that, in stage (a), poly(1,4-α-D-glucans) are used as starting materials which have been produced from biotransformation, from reaction with enzymes or from reaction of sucrose with an enzyme having the enzymatic activity of an amylosucrase; see, for example, WO 95 31 553.

An amylosucrase is taken to mean an enzyme that catalyzes the following reaction:

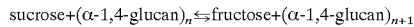

Starting from this reaction scheme, linear oligomeric or polymeric α-1,4-glucans can serve as acceptors for a chain-extending reaction which leads to water-insoluble poly(1,4-α-D-glucans), whose glucose radicals are linked by α-1,4-glycosidic bonds and which have a molecular weight In the range from $0.75 \times 10^2$ g/mol to $10^7$ g/mol.

The linear oligomeric or polymeric acceptors can either be added from external sources, but can also be produced from sucrose, as described in example 1, by the amylosucrase itself.

α-1,6-Glycosidic bonds cannot be detected in these products by $^{13}$C-NMR (Remaud-Simeon et al. in Carbohydrate Bioengineering (ed. S. B. Petersen et al.), Elsevier Science B. V. (1995), 313–320).

Water-insoluble poly(1,4-α-D-glucans) which have the above-described properties, but have been produced in different ways, can also be starting materials of the inventive process.

In a further preferred embodiment of the inventive process, water-insoluble poly(1,4-α-D-glucans) are used as starting materials which can be produced by reacting sucrose with an enzyme having the enzymatic activity of an amylosucrase, with the use of branched polysaccharide acceptors, for example glycogen, amylopectin, dextrin. The amylosucrase catalyzes an α-1,4-glucan chain extension of these branched polysaccharide acceptors. The resultant water-insoluble poly(1,4-α-D-glucans), in comparison with the branched polysaccharide acceptors used, have a lower degree of branching. These products are also termed poly (1,4-α-D-glucans) in the context of the present invention.

Such water-insoluble poly(1,4-α-D-glucans) which have the above-described properties, but have been produced in other ways, can also be starting materials of the inventive process.

In addition, the embodiments of the Inventive process can be characterized in that the water-insoluble poly(1,4-α-D-glucans) are chemically modified in a manner known per se.

In addition, the embodiments of the inventive process can be characterized in that the water-insoluble poly(1,4-α-D-glucans) have a degree of branching in the 6 position of at most 0.5%.

In addition, the embodiments of the inventive process can be characterized in that the water-insoluble poly(1,4-α-D-glucans) have a degree of branching in the 2 or 3 position of, in each case, at most 1%, and in particular at most 0.5%.

In addition, the embodiments of the inventive process can be characterized in that the water-insoluble poly(1,4α-D-glucans) have a molecular weight of from $0.75 \times 10^2$ to $10^7$, preferably from $10^3$ to $10^6$ and preferably from $10^3$ to $5 \times 10^5$ g/mol.

In addition, the embodiments of the inventive process can be characterized in that the water-insoluble poly(1,4-α-D-glucans) have neither been debranched, in particular have neither been enzymatically debranched, nor have been reduced with respect to their chain length (and thus with respect to their molecular weight), in particular not by enzyme catalysis, acid catalysis, extrusion, oxidation or pyrolysis.

The term "high RS content" is taken to mean an RS content of at least 25%, preferably from 65 to 75, from 75 to 88, from 88 to 90, from 90 to 95, and in particular from 95 to 99%/o by weight or more.

Thus, the embodiments of the inventive process can be characterized in that α-amylase-resistant polysaccharides are produced having an RS content of at least 65% by weight.

In addition, the embodiments of the inventive process can be characterized in that, in the drying steps (e) and (d), the retrograded product is dried by spray-drying or freeze-drying.

A further embodiment of the invention relates to the use of an inventive α-amylase-resistant polysaccharide for intermediate food products or foods.

A further embodiment of the invention relates to the use of an inventive α-amylase-resistant polysaccharide as food additive.

Finally, an embodiment of the invention relates to an intermediate food product or food, characterized by a content of an inventive α-amylase-resistant polysaccharide.

The examples below serve to illustrate the invention in more detail without restricting it to these examples.

EXAMPLE 1

Biotransformation 5 l of a sterilized 30% sucrose solution are placed in a 5-l vessel. An enzyme extract containing an amylosucrase from Neisseria polysaccharea (see WO 9531 553) is added in one portion and mixed. The enzyme activity used is 148,000 units in this experiment, The sealed vessel was incubated at 37° C. During the biotransformation, a white precipitate forms The reaction Is terminated after 39 h. The precipitate is centrifuged off, frozen at −7000 and then freeze-dried. The mass of the freeze-dried solid is 526.7 g (70.2% yield).

To separate off low-molecular-weight sugars, 200 g of the solid are washed with water at room temperature with stirring for 30 min, frozen at −70° C. and freeze-dried. The fructose and sucrose contents are determined by a coupled enzymatic assay , after dissolving the solid in DMSO, and the fructose content is 4.61 mg per 100 mg of solid (4.6%). The sucrose content is below the limit of detection.

The supernatant of the biotransformation is denatured at 95° C. After cooling to room temperature, it was centrifuged again, The clear supernatant was frozen at −70° C. and thawed at 4° C. over 3 days. The precipitate thus produced was frozen at −70° C. and freeze-dried.

To separate off low-molecular-weight sugars, 39.5 g of the solids are washed at room temperature with water for 30 min with stirring, frozen at −70° C. and freeze-dried The contents of fructose and sucrose are determined by a coupled enzymatic assay according to STITT et al. (Meth. Enzym., 174 (1989) 518–552), after dissolving the solids in DMSO, and the fructose content is 2.27 mg per 100 mg of solids. The sucrose content is below the limit of detection.

EXAMPLE 2

Starting Material

Determination of the molecular weight of the water-insoluble poly-(1,4-α-D-glucan) synthesized using amylosucrase, from example 1 (FIG. 1).

2 mg of the poly(1,4-α-D-glucan) from example 1 are dissolved at room temperature in dimethyl sulfoxide (DMSO, analytical grade, from Riedel-de-Haen) and filtered (2 μm), One portion of the solution is passed into a gel-permeation chromatography column. The eluent used is DMSO. The signal intensity is measured using an RI detector and evaluated against pullulan standards (from Polymer Standard Systems). The flow rate is 1.0 ml per minute.

The measurement gives a number average molecular weight ($M_n$) of 2326 g/mol and a weight average molecular weight ($M_w$) of 3367 g/mol. The recovery rate is 100%.

EXAMPLE 3

Example for Determination of the RS Content 200 mg (dry weight) of a pulveruent product to be analyzed for its RS content were incubated at pH 5.2 for 120 min to determine the RS content using the enzyme mixture described, according to the method of Englyst et al. (Eur. J. Clin. Nutrition, 46 (1992) (Suppl. 2) pp. 33–550). After termination of the enzymatic degradation, the enzyme activity was stopped by reducing the pH to a value of 3 and the temperature to 20° C. Then, by adding 4 times the amount of ethanol, the mixture was adjusted to an 80% (v/v) ethanolic solution. The 80% ethanolic solution was allowed to stand for 1 h at room temperature. The precipitate was centrifuged (2500× g, 10 min) and the supernatant was discarded. The residue was washed three times with 80% (v/v) ethanol and once with absolute ethanol and centrifuged. The residue was lyophilized and weighed. The dry mass of the residue was determined and the RS content calculated from the following equation:

RS[%]=100×weight of the residue (dry weight)/initial weight (dry weight)

EXAMPLES 4 to 7

A linear nature-identical poly(1,4α-D-glucan) (see example 1) was heated in aqueous solution and a gel was formed. This gel was adjusted to 10% by weight solids content and portioned. The portions were retrograded at 4 and 25° C. (example 5 and 6) or using a step program (example 7). In addition, the linear carbohydrate polymer from the reaction solution was frozen out (example 4). The retrograded samples were dried and the RS content determined as described above.

Table 2 illustrates the effect of the retrogradation temperature and retrogradation conditions on the RS content in the product which is prepared from a 10% gel of the poly(1,4α-D-glucans) used by retrogradation for 24 hours.

TABLE 2

| Example | Retrogradation temperature | RS [% by weight] |
| --- | --- | --- |
| 4 | −70° C. | 78 ± 4 |
| 5 | 4° C. | 70 ± 2 |
| 6 | 25° C. | 87 ± 1 |
| 7 | Step program | 74 ± 3 |

This example in table 2 shows that the retrogradation temperature affects the RS content. Thus retrogradation at 25° C. leads to a significantly higher RS content compared with retrogradation at 4° C. In contrast, retrogradation at −70° C. produces a slightly higher RS content than retrogradation at 4° C. The starting product behaves accordingly differently from maltodextrins, as described and claimed in EP 0 688 872 A1.

EXAMPLES 8 to 12

The same poly(1,4α-D-glucan) used as under examples 4 to 7 was heated in aqueous solution to form a gel. This gel was adjusted to 10 and 30% by weight solids content and portioned. The portions were retrograded at 4 and 25° C. or using a stepped program. Table 3 illustrates the effect of the solids content in the gel of the RS content in the product produced from 10% and 30% gel of the poly(1,4-α-D-glucan) used by 24 hour retrogradation.

TABLE 3

| Example | Retrogradation temperature | Solids content 10% RS [% by weight] | 30% RS [% by weight] |
| --- | --- | --- | --- |
| 8 | 4° C. | 70 ± 2 | |
| 9 | 4° C. | | 94 ± 2 |
| 10 | 25° C. | 87 ± 1 | |
| 11 | 25° C. | | 93 ± 1 |
| 12 | stepped program | 74 ± 3 | |

This example in table 3 shows that the solids content in the gel affects the RS content. Thus retrogradation of 30% solids content leads to a significantly higher RS content in the product compared with retrogradation at 10% solids content. The starting product therefore behaves differently from maltodextrins, as described and claimed in EP 0 688 872 A1.

EXAMPLES 13 to 21

The same poly(1,4-α-D-glucan) used as under examples 4 to 7 was heated in aqueous solution to form a gel, This gel was adjusted to 10 and 30% by weight solids content and portioned, The portions were retrograded at −70, 4 and 25° C. The resultant products were then dried and the thermal stability was studied using differential scanning calorimetry (DSC).

The DSC measurement gives an endothermic peak for the swelling of native starch. The same also applies for retrograded starches and poly(1,4-α-D-glucans). The processes of melting of the crystallites, conformation change and hydration and swelling of starch polymers may be characterized from endotherms.

Measurements under the condition of water excess (water contents above 60%) generally give a uniform peak. This peak is characterized by various parameters, such as onset temperature $T_0$, peak temperature $T_p$, end temperature $T_c$, and reaction enthalpy dH (peak area). The abovementioned condition is satisfied for all parameters listed in table 4.

The measurements were carried out with a high-resolution instrument (DSC 120, Seiko, Japan). The glucan/water ratio was 1:5, the heating rate 4 K/min. The measurement was carried out in a temperature range from 10 to 220° C. The instrument operates according to the heat flux measurement principle. Per measurement, 5 mg of polyglucan were weighed using an ultramicrobalance into silver crucibles of 70 μl capacity and these were then hermetically sealed after addition of distilled water. The reference sample used was distilled water having a conductivity of 0.15 μS.

TABLE 4

| Name Poly(1,4-α-D-glucan) Example | Retrogradation conditions temperature/solids content in the gel | DSC parameter | | | |
|---|---|---|---|---|---|
| | | $T_o$ [°C.] | $T_p$ [°C.] | $T_c$ [°C.] | dH [J/g] |
| 13 | low-temperature recrystallization | 85.1 | 102.0 | 111.3 | 21.8 |
| 14 | 4° C., 10% | 81.8 | 96.7 | 108.0 | 16.3 |
| 15 | 4° C., 30% | 56.2 | 98.2 | 103.7 | 1.8 |
| 16 | | 109.3 | 124.5 | 136.8 | 13.3 |
| 17 | | 142.7 | 154.1 | 165.6 | 2.9 |
| 18 | 25° C., 10% | 88.6 | 101.0 | 109.8 | 15.0 |
| 19 | 25° C., 30% | 85.9 | 97.9 | 101.1 | 1.7 |
| 20 | | 111.8 | 128.1 | 133.9 | 4.0 |
| 20 | | 138.1 | 157.6 | 172.5 | 23.0 |

These examples in table 4 show that the solids content in the gel affects the thermal stability of the retrograded products. Thus retrogradation at 30 % solids content in the gel leads to products which exhibit endotherms having more than one peak in DSC measurements, with peak temperatures ($T_p$) of >120° C. occurring in these endotherms. In contrast, retrogradation of 10% gel leads to products whose endotherms only have peak with $T_p$ values between 95 and 100° C. Increasing the solids content in the gel thus increases the thermal stability of the retrograded product.

EXAMPLE 22

Determination of the Solubility of Polysaccharides and Classification According to the German Pharmacopeia (DAB)

564 mg of poly(1,4-α-glucan) (see example 1) are heated in approximately 0.5 l of twice-distilled water at 1.3 bar and 130° C. for 1.5 hours in an autoclave (*Certoclav apparatus*). The weight of the reaction vessel has been measured in advance. The apparatus is then depressurized and cooled at room temperature. The contents are weighed. This corresponds to 501.74 g. After a further 24 hours, the contents are centrifuged and decanted. The solid residue is dried and weighed. There are 468 mg. A dissolved portion of 96 mg is calculated from this. Based on the solvent used, it is calculated therefrom that 5226 mg of water are necessary for 1 mg of poly(1,4-α-D-glucan). According to the classification of the DAB, this classifies the substance as "very sparingly soluble", since between 1000 and 10000 parts of solvent are necessary to dissolve 1 part of the substance. This is class number 6 of the 7 classes for classifying solubility (from "very highly soluble" (class 1) to "virtually insoluble" (class 7)).

EXAMPLE 23

Determination of the Solubility of Polysaccharides and Classification According to the German Pharmacopeia (DAB)

The experiment is carried out as in Example 22. The sole difference is the cooling process which is provided downstream of the autoclave treatment and cooling to room temperature. The substance mixture is kept at 5° C. for 3 hours.

526 mg of poly(1,4-α-D-glucan) are weighed into approximately 480 ml of twice-distilled water. After the thermal treatment, a weight of 468.09 g results. The dried sediment is 488 mg. Therefore, 39 mg of the poly(1,4-α-glucan) have dissolved. This corresponds to a ratio of 1 mg of substance to 12 305 parts of solvent. Therefore, the substance according to this treatment method must be classified in class number 7 according to DAB and therefore as virtually insoluble, because more than 10 000 of solvent are required for one part of substance.

What is claimed is:

1. A composition comprising an α-amylase-resistant retrograded polysaccharide having an RS content of at least 75% by weight, obtainable by a process comprising:
   (a) obtaining a water-insoluble poly(1,4-α-D-glucan) by a reaction of sucrose with an enzyme having the activity of an amylosucrase;
   (b) producing a mixture comprising said poly(1,4-α-D-glucan) and water;
   (c) warming the mixture to provide a gel;
   (d) cooling the resulting gel and allowing retrogradation of the gel at a temperature which is lower than the temperature of the heated gel; and
   (e) optionally drying or dewatering the resulting product.

2. The α-amylase-resistant polysaccharide of claim 1 wherein the poly(1,4-α-D-glucan) has been chemically modified.

3. The α-amylase-resistant polysaccharide of claim 1 wherein the degree of branching at the 6 position is at most 0.5%.

4. The α-amylase-resistant polysaccharide of claim 3 wherein the degree of branching at the 2,3 or both positions is at most 1.0% in each case.

5. The α-amylase-resistant polysaccharide of claim 1 wherein the water insoluble poly(1,4-α-D-glucan) has neither been debranched nor reduced with respect to its chain length.

6. A composition comprising an α-amylase-resistant retrograded polysaccharide having an RS content of at least 75% by weight, obtainable by a process comprising:
   (a) obtaining a water-insoluble poly(1,4-α-D-glucan) by a reaction of sucrose with an enzyme having the activity of an amylosucrase;
   (b) producing a suspension or dispersion comprising said poly(1,4-α-D-glucan) and water;
   (c) freezing the resultant suspension or dispersion;
   (d) allowing retrogradation to proceed;
   (e) thawing the mass obtained by step (d); and
   (f) optionally drying or dewatering the resultant mass.

7. A process for producing an α-amylase-resistant polysaccharide having an RS content of at least 75% by weight, comprising:
   (a) obtaining a water-insoluble poly(1,4-α-D-glucan) by a reaction of sucrose with an enzyme having the activity of an amylosucrase;
   (b) producing a mixture comprising said poly(1,4-α-D-glucan) and water;
   (c) warming the mixture to provide a gel;
   (d) cooling the resulting gel and allowing retrogradation of the gel at a temperature which is lower than the temperature of the heated gel; and
   (e) optionally drying or dewatering the resultant product.

8. The process of claim 7 wherein the mixture produced in step (b) has a polysaccharide content of at least about 5% and up to about 50% by weight.

9. The process of claim 7 wherein, in step (c), the gel is warmed or heated to a temperature in the range from room temperature to 100° C.

10. The process of claim 7 wherein, in step (d), retrogradation proceeds
(i) at a temperature in the range from 50° C. to the freezing point; and
(ii) for a time interval from 1 to 72 hours.

11. A process for producing an α-amylase-resistant polysaccharide having an RS content of at least 75% by weight, comprising:
(a) obtaining a water-insoluble poly(1,4-α-D-glucan) by a reaction of sucrose with an enzyme having the activity of an amylosucrase;
(b) producing a suspension or dispersion comprising said poly(1,4-α-D-glucan) and water;
(c) freezing the resultant suspension or dispersion;
(d) allowing retrogradation to proceed;
(e) thawing the mass obtained by step (d); and
(f) optionally drying or dewatering the resultant mass.

12. The process of claim 11 wherein, in step (c), the resultant suspension or dispersion is cooled to a temperature in the range from 0° C. to −80° C.

13. The process of claim 11 wherein, in step (d), retrogradation is allowed to proceed for a time interval of from 1 to 72 hours.

14. The process of claim 7 wherein the water-insoluble poly(1,4-α-D-glucan) has been chemically modified.

15. The process of claim 7 wherein the water-insoluble poly(1,4-α-D-glucan) has a degree of branching at the 6 position of at most 0.5%.

16. The process of claim 7 wherein the water-insoluble poly(1,4-α-D-glucan) has a degree of branching at the 2,3 or both positions of at most 1.0% in each case.

17. The process of claim 7 wherein the water insoluble poly(1,4-α-D-glucan) has neither been debranched nor reduced with respect to its chain length.

18. The process of claim 7 wherein, in step (e), the resultant product is dried by spray-drying or freeze-drying.

19. An intermediate food product or food comprising an α-amylase-resistant retrograded polysaccharide prepared according to claim 7.

* * * * *